April 2, 1963 G. J. VON ABRAMS Plant Pat. 2,245
ROSE PLANT
Filed Jan. 9, 1962
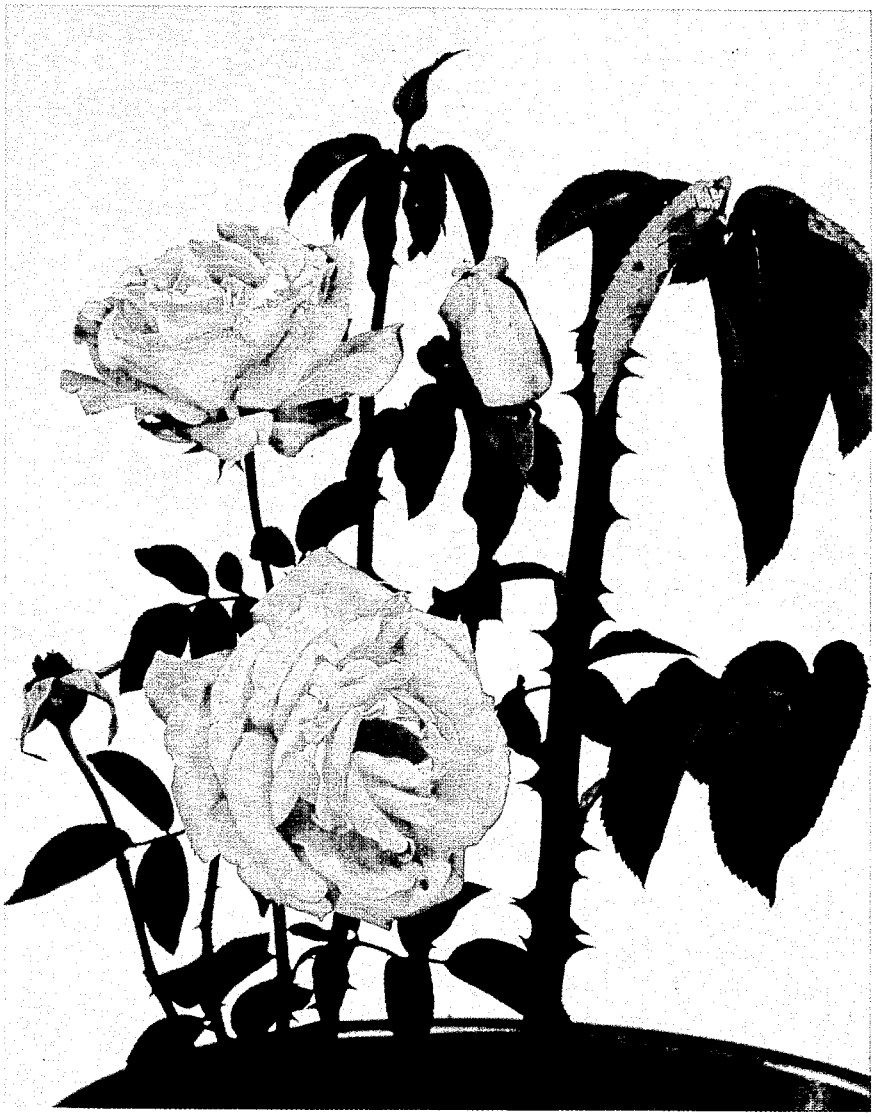
INVENTOR.
GORDON J. VON ABRAMS
BY F. A. Geisler
ATTORNEY

United States Patent Office

Plant Pat. 2,245
Patented Apr. 2, 1963

2,245
ROSE PLANT

Gordon J. Von Abrams, 3463 NW. Savier St., Portland, Oreg.

Filed Jan. 9, 1962, Ser. No. 165,266
1 Claim. (Cl. 47—61)

This invention comprises a new and distinct variety of rose plant of the commercial "hybrid tea" class. In the pollination which took place in the breeding of this new variety the seed parent had been produced by crossing the rose variety "Charlotte Armstrong" (Plant Patent No. 455) with the rose variety "Mme. Henri Guillot" (Plant Patent No. 337) and the pollen parent by crossing the rose variety "Multnomah" (Plant Patent No. 883) with the rose variety "Charles Mallerin" (Plant Patent No. 933).

The main objective of this particular breeding was to develop a new variety of rose which would produce flowers having a strong fragrance and a distinct soft reverse-bicolor flower color. This objective was achieved.

The pollination took place at Scappoose, Oregon, in the spring of 1953 and was performed by me. Subsequent asexual propagation at the same location was performed by bud-grafting. This new variety of rose has been shown to retain its initial distinguishing characteristics through repeated vegetative reproductions by bud-grafting.

This new variety of rose is not similar to any other variety of rose in commerce known to me. The closest comparison would, I believe, be with the rose variety "Angel Wings" (Plant Patent No. 1,865); but the open flowers of the latter are more yellow in color, less fragrant, with fewer petals, the flower buds are lighter colored, more pointed and longer, the plant is taller, and the foliage is less glaucous, than is the case with this new variety of rose.

The new variety originated as a seedling, and is a medium tall bush type. It is particularly suitable for use outdoors, for garden decoration and for cut-flowers. The flowers have an intense pleasing fragrance, and have a distinct color combination and flower form, as described in detail hereinafter. The light color and grayish appearance of the foliage of the plant adds further to its distinctiveness.

The accompanying illustration was made from specimens grown outside at Scappoose, Oregon, during July 1960, the colors shown being as nearly true as is reasonably possible in a color reproduction of this type.

In the more detailed description which follows, these color references are used:

(1) Wilson, R. F.—Royal Horticultural Society Colour Chart, England, 1940 (abbreviated "W").

(2) Ridgway, R.—Color Standards and Color Nomenclature, Washington, D.C., 1912 (abbreviated "R").

*Flowers*

The flowers are borne one to three or four per main stem, on moderately long strong stems. The plant blooms abundantly outdoors and blooms nearly continuously during the growing season.

Open flower:

*Size.*—Large (to 6 inches).

*Petalage.*—Double; ca. 30 to 50 petals.

*Form.*—High-centered at first, becoming cup shaped with full flat center. Petals at first lightly rolled outward at margins, later ruffled, gradually rolling outward at apex or apical-lateral margins.

*Fragrance.*—Very intense, fruity.

Petals:

*Substance.*—Thick, firm, flexible.

*Texture.*—Outside shiny; inside satiny.

*Shape and size (in open flower).*—Outer petal—broadly obovate (i.e.—5.5 cm. high x 6.2 cm. wide). Intermediate petal—broadly obovate (i.e.—4.5 cm. high x 4.2 cm. wide). Inside petal—somewhat irregular; obovate (i.e.—4 x 3.3 cm.).

Color: Following description of newly opened flower made in August 1960, from specimens grown outdoors near Scappoose, Oregon:

*Outside petal.*—Outer surface—very small yellow mark at point of attachment; base white, or near-white, blending gradually upward to near Fuchsine Pink (W. 627/2, p. 78). Inner surface—small yellow mark at point of attachment; base white or near-white, blending shortly upward to near Solferino Purple (W. 26/1 to 26, p. 26).

*Inside petal.*—Outer surface—slight yellow flush at base, blending shortly with near Phlox Pink (W. 625/2, p. 77). Inner surface—small yellow fan at base near Sulphur Yellow (W. 1, p. 1) blending shortly above to near-white, which merges shortly above to near Rose Bengal (W. 25/1 to 25 p. 25).

*General color effect.*—Near Rose Bengal (W. 25/1, p. 25) with silvery-white under-side.

The following description of a flower open three days in August 1960, was made from specimens grown near Scappoose, Oregon:

*Outside petal.*—Outer surface—white or near-white at base, blending gradually upward to near Fuchsine Pink (W. 627/2, p. 78). Inner surface—small pale yellow mark at point of attachment; base white or near-white, blending upward to near Solferino Purple (W. 26/1, p. 26).

*Inside petal.*—Outer surface—base white or near-white, blending and merging upward (sometimes in streaks) to near Fuchsine Pink (W. 627/2, p. 78) or whiter. Inner surface—base white, or near-white, blending upward to near Solferino Purple (W. 26/1 to 26, p. 26).

*General color effect.*—Near Solferino Purple (W. 26/2, p. 26).

Behavior in senescence: Petals drop cleanly. Color becomes gradually more blue and less intense, particularly at relatively high temperatures.

Flower longevity: Ordinary.

Bud:

*Peduncle.*—Size—medium (i.e.—6. cm. x 2.5 mm.); strength erect; color near Scheele's Green (W. 860/3, p. 175) variably flushed red; surface with numerous glandular cilia.

*Sepals.*—Size—Ordinary; form spear-shape. Point—aristate to moderately foliaceous. Lateral margins—most with numerous glandular cilia and few bristle-like appendages. Surface—outer moderately rough, glandular, pubescent; inner lightly tomentose. Color—outer surface near Scheele's Green (W. 860/2, p. 175) variably flushed near Bordeaux (R. 71. V-RR. *k*, Plate XII); inner surface near Light Flourite Green (R. 33″. GY-G. *d*, Plate XXXII). Behavior—reflex normally.

*Before calyx breaks.*—Size—medium. Form—medium pointed, with moderate foliaceous terminal points. Surface—rough, glandular, with few bristle-like appendages.

*As calyx breaks.*—Exposed petal color near Eugenia Red (R. 1′. RED, Plate XIII) or darker.

*As first petal opens.*—Size of bud—medium (i.e.—ca. 2.5 x 3.5 cm.). Form of bud—medium pointed.

Color of petal—outside near Solferino Purple (W. 26/2 to 26/3, p. 26); inside near Solferino Purple W. 26, p. 26), or darker.

*Opening habit.*—Normal.

*Plant*

Foliage:

*Leaves.*—Compound; 5 to 7 leaflets; abundant; large.

*Leaflets.*—Substance—thick, hard, stiff. Texture—moderately smooth; dull; often glaucous. Size—large (i.e., terminal leaflet ca. 6 x 10 cm.). Shape—ovate; base rounded; apex acuminate; margin serrate. Color: mature—upper surface near Spinach Green (W. 0960, p. 187); under surface near Chromium Green (R. 31″. Y-G. *i*, Plate XXXII); often appears dusty and grayish; young—upper surface near Roman Green (R. 23′ YELLOW. *m*, Plate XVI) flushed red along mid-rib and margins; under surface near Indian Red (R. 3″. O-R. *k*, Plate XXVII).

*Rachis.*—Caliber—medium heavy. Upper side—groove narrow; ridges with few glandular cilia. Under side—few small thorns; very few gland-tipped cilia.

*Stipules.*—Size—medium (i.e.—8 x 20 mm.). Points—medium long, slender; sometimes flared outward, but usually straight and turned out at an angle less than 45°. Margins—very glandular, with irregular dentation.

*Disease resistance.*—Ordinary, susceptible to "powdery mildew."

Growth:

*Habit.*—Medium-tall, upright, well-branched.

*Vigor.*—Moderate.

*Canes (in second year of growth).*—Caliber—heavy. Surface—rough, corky; thorns small, grayish, very numerous. General color—gray, very little green.

*Main stems (of current year's growth).*—Caliber—medium. Surface—glaucous, somewhat rough, with several long narrow corky lenticels; thorns numerous, medium size, grayish tan, nearly straight; base oval. Color—near Light Elm Green (R. 27′. G-Y. *k*, Plate XVII).

*Branches (currently bearing fruit or senescent flowers).*—Caliber—medium. Surface—moderately smooth; glaucous; thorns numerous; medium size; hooked downwardly; color reddish; base oval; cilia numerous; glandular, reddish. Color—near Asphodel Green (R. 29‴. GG-Y., Plate XLI).

*New shoots (in rapid growth).*—Surface—smooth; slightly glaucous; thorns many; medium size; hooked sligthtly downward; color reddish; base narrow oval; cilia several; glandular. Color—near Biscay Green (R. 27′. G-Y. *i*, Plate XVII), heavily over-flushed near Vinaceous-Brown (R. 5‴. OO-R. *i*, Plate XXXIX).

*Reproductive Organs*

Stamens:

*Quantity.*—Moderate.

*Position.*—Normal, immediately within corolla.

*Filaments.*—Medium-short, pale, nearly all with anthers.

*Anthers.*—Size ordinary; yellow.

*Pollen.*—Abundant; viability good.

Pistils:

*Quantity.*—Numerous.

*Styles.*—Length moderate (i.e.—1 cm.); contorted; tightly bunched; basal ⅓ with dense cottony tissue.

*Stigmas.*—Small, grayish.

*Ovaries.*—Enclosed.

Receptacle and calyx-tube:

*Size.*—Small.

*Shape.*—Turbinate.

*Disc.*—Inconspicuous.

*Surface.*—Glossy.

*Color.*—Near Scheele's Green (R. 33. GY-G. *i*, Plate VI).

Fruit ("seed-pod"):

*Quantity.*—Few.

*Size.*—Medium.

*Shape.*—Globular.

*Sepals.*—Persistent.

*Surface.*—Smooth.

*Wall.*—Medium thick, fleshy.

*Color.*—Variable orange at maturity.

Seeds: Moderate number, large, viable.

Having thus described my invention, I claim:

A new and distinct variety of rose plant of the commercial "hybrid tea" class characterized by the intense pleasing fragrance of the flowers, and by the soft reverse-bicolored flowers and unusual flower form, as herein shown and described.

No references cited.